US009466877B2

(12) United States Patent
Dixon et al.

(10) Patent No.: US 9,466,877 B2
(45) Date of Patent: Oct. 11, 2016

(54) HOSPITAL BED HAVING NEAR FIELD COMMUNICATION CAPABILITY

(71) Applicants: Steven A. Dixon, Cincinnati, OH (US); Keith A. Huster, Sunman, IN (US); Irvin J. Vanderpohl, III, Greensburg, IN (US); Thomas F. Heil, Batesville, IN (US); Richard J. Schuman, Cary, NC (US); Christopher K. Lack, Milan, IN (US)

(72) Inventors: Steven A. Dixon, Cincinnati, OH (US); Keith A. Huster, Sunman, IN (US); Irvin J. Vanderpohl, III, Greensburg, IN (US); Thomas F. Heil, Batesville, IN (US); Richard J. Schuman, Cary, NC (US); Christopher K. Lack, Milan, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 616 days.

(21) Appl. No.: 13/687,005

(22) Filed: Nov. 28, 2012

(65) Prior Publication Data
US 2013/0135160 A1    May 30, 2013

Related U.S. Application Data

(60) Provisional application No. 61/564,466, filed on Nov. 29, 2011.

(51) Int. Cl.
| | | |
|---|---|---|
| *H01Q 1/12* | (2006.01) | |
| *H01Q 1/44* | (2006.01) | |
| *H01Q 1/00* | (2006.01) | |
| *A61B 5/00* | (2006.01) | |

(52) U.S. Cl.
CPC ............... *H01Q 1/44* (2013.01); *H01Q 1/007* (2013.01); *A61B 5/002* (2013.01); *A61B 5/6891* (2013.01)

(58) Field of Classification Search
CPC ........ H01Q 1/44; H01Q 1/007; A61B 5/002; A61B 5/6891
See application file for complete search history.

(56) References Cited

U.S. PATENT DOCUMENTS

| | | | |
|---|---|---|---|
| 5,398,149 A | 3/1995 | Weil | |
| 5,561,412 A | 10/1996 | Novak et al. | |
| 5,699,038 A * | 12/1997 | Ulrich et al. | 340/286.07 |

(Continued)

FOREIGN PATENT DOCUMENTS

WO    2005/022692 A3    3/2005

OTHER PUBLICATIONS

"Texas Instruments Announces the New TRF7970A NFC Contactless Short-Range Communication Transceiver." Embedded System News.Com, http://embeddedsystemnews.com/texas-instruments-ammounces-the-new-trf7970a-nfc-contactless . . . ; printed Nov. 22, 2011.

(Continued)

*Primary Examiner* — Trinh Dinh
(74) *Attorney, Agent, or Firm* — Barnes & Thornburg LLP

(57) ABSTRACT

An apparatus for providing data communication and power to a device located in a room having a power outlet is disclosed. The power outlet may be a standard AC outlet, for example. The apparatus includes a cable extending from the device and having a plug comprising a plug body. Prongs extend from the plug body and couple to the power outlet to receive power. A first near field communication antenna is carried by the plug body. A communication module has a second near field communication antenna and is located in the room in proximity to the plug. At least one of the first near field communication antenna and the second near field communication antenna communicates data wirelessly to the other of the first near field communication antenna and the second near field communication antenna.

14 Claims, 3 Drawing Sheets

(56) References Cited

U.S. PATENT DOCUMENTS

| | | | |
|---|---|---|---|
| 5,838,223 A | 11/1998 | Gallant et al. | |
| 6,147,592 A | 11/2000 | Ulrich et al. | |
| 6,362,725 B1 | 3/2002 | Ulrich et al. | |
| 6,721,980 B1 | 4/2004 | Price et al. | |
| 6,735,430 B1 | 5/2004 | Farley et al. | |
| 6,897,780 B2 | 5/2005 | Ulrich et al. | |
| 7,242,308 B2 | 7/2007 | Ullrich et al. | |
| 7,319,386 B2 | 1/2008 | Collins, Jr. et al. | |
| 7,330,127 B2 | 2/2008 | Price et al. | |
| 7,375,616 B2 | 5/2008 | Rowse et al. | |
| 7,399,205 B2 | 7/2008 | McNeeley et al. | |
| 7,515,059 B2 | 4/2009 | Price et al. | |
| 7,538,659 B2 | 5/2009 | Ulrich et al. | |
| 7,552,879 B2 | 6/2009 | Nagata et al. | |
| 7,590,384 B2 | 9/2009 | Dawidowsky | |
| 7,652,578 B2 | 1/2010 | Braun et al. | |
| 7,688,270 B2 | 3/2010 | Tsushima | |
| 7,706,559 B2 | 4/2010 | Collins, Jr. et al. | |
| 7,734,307 B2 | 6/2010 | Dawidowsky | |
| 7,737,827 B2 | 6/2010 | Perkins et al. | |
| 7,746,218 B2 | 6/2010 | Collins, Jr. et al. | |
| 7,751,375 B2 | 7/2010 | Perkins et al. | |
| 7,756,467 B2 | 7/2010 | Bent et al. | |
| 7,768,949 B2 | 8/2010 | Perkins et al. | |
| 7,899,393 B2 | 3/2011 | Luong | |
| 7,907,926 B2 | 3/2011 | Rofougaran | |
| 7,912,441 B2 | 3/2011 | Von Bosch | |
| 7,929,910 B2 | 4/2011 | Chen | |
| 7,937,107 B2 | 5/2011 | Rofougaran et al. | |
| 7,941,096 B2 | 5/2011 | Perkins et al. | |
| 7,995,971 B2 | 8/2011 | Rofougaran et al. | |
| 8,013,717 B2 | 9/2011 | Alberth, Jr. et al. | |
| 8,014,720 B2 | 9/2011 | Lortz | |
| 8,014,721 B2 | 9/2011 | Johnson | |
| 8,041,227 B2 | 10/2011 | Holcombe et al. | |
| 8,060,012 B2 | 11/2011 | Sklovsky et al. | |
| 8,086,176 B2 | 12/2011 | Teruyama et al. | |
| 8,096,813 B2 | 1/2012 | Biggs | |
| 8,099,045 B2 | 1/2012 | Chang | |
| 8,108,684 B2 | 1/2012 | Addy | |
| 8,115,598 B2 | 2/2012 | Rofougaran et al. | |
| 8,116,679 B2 | 2/2012 | Dunko | |
| 8,116,680 B2 | 2/2012 | Bloebaum et al. | |
| 8,117,445 B2 | 2/2012 | Werner et al. | |
| 8,145,140 B2 | 3/2012 | Rofougaran et al. | |
| 8,150,374 B2 | 4/2012 | Lowe | |
| 8,150,915 B1 | 4/2012 | Raman et al. | |
| 8,175,533 B2 | 5/2012 | Schubert | |
| 8,180,285 B2 | 5/2012 | Rofougaran | |
| 8,180,289 B1 | 5/2012 | Glickman | |
| 8,185,047 B2 | 5/2012 | Washiro | |
| 8,212,735 B2 | 7/2012 | Hyvonen et al. | |
| 8,213,860 B2 | 7/2012 | Teruyama et al. | |
| 8,224,246 B2 | 7/2012 | Suumaki et al. | |
| 8,232,882 B2 | 7/2012 | Miyabayashi et al. | |
| 8,233,841 B2 | 7/2012 | Griffin et al. | |
| 8,238,825 B2 | 8/2012 | Rofougaran et al. | |
| 8,249,524 B2 | 8/2012 | Darwhekar et al. | |
| 8,249,650 B2 | 8/2012 | Rofougaran et al. | |
| 8,266,027 B2 | 9/2012 | Moritz et al. | |
| 8,272,892 B2 | 9/2012 | McNeely et al. | |
| 8,280,304 B2 | 10/2012 | Hirsch | |
| 8,289,716 B2 | 10/2012 | Patel et al. | |
| 8,291,091 B2 | 10/2012 | Naniyat | |
| 8,311,479 B2 | 11/2012 | Teruyama et al. | |
| 8,311,504 B2 | 11/2012 | Rofougaran | |
| 8,321,922 B1 | 11/2012 | Lo et al. | |
| 8,326,281 B2 | 12/2012 | Hill | |
| 8,355,670 B2 | 1/2013 | White | |
| 8,368,540 B2 | 2/2013 | Perkins et al. | |
| 8,369,889 B2 | 2/2013 | Rofougaran et al. | |
| 8,380,977 B2 | 2/2013 | Son et al. | |
| 2007/0141869 A1* | 6/2007 | McNeely et al. | 439/76.1 |
| 2008/0155257 A1 | 6/2008 | Werner et al. | |
| 2008/0224861 A1* | 9/2008 | McNeely et al. | 340/540 |
| 2009/0212925 A1 | 8/2009 | Schuman, Sr. et al. | |
| 2009/0212956 A1 | 8/2009 | Schuman et al. | |
| 2009/0214009 A1 | 8/2009 | Schuman, Sr. et al. | |
| 2009/0217080 A1 | 8/2009 | Ferguson et al. | |
| 2009/0325484 A1 | 12/2009 | Lele et al. | |
| 2010/0007498 A1 | 1/2010 | Jackson | |
| 2010/0101022 A1 | 4/2010 | Riley et al. | |
| 2010/0182153 A1 | 7/2010 | Jensen | |
| 2011/0068892 A1 | 3/2011 | Perkins et al. | |
| 2011/0070833 A1 | 3/2011 | Perkins et al. | |
| 2011/0201270 A1 | 8/2011 | Perkins et al. | |
| 2011/0207402 A1 | 8/2011 | Perkins et al. | |
| 2012/0007717 A1* | 1/2012 | Jong | G02B 6/3895 340/10.4 |
| 2012/0264374 A1 | 10/2012 | Perkins et al. | |
| 2012/0324119 A1 | 12/2012 | Imes et al. | |
| 2013/0318716 A1* | 12/2013 | Vanderpohl, III | 5/600 |

OTHER PUBLICATIONS

"Multi-Protocol Fully Integrated 13.56 MHz RFIA/Near Field Communication (NFC) Transceiver IC," TRF7970A, 85 pages, Aug. 2011—Revised Jan. 2013.

"TRF7970A Near Field Communication Transceiver IC," © 2011 Texas Instruments Incorporated, 3 pages.

EP Search Report on Application No. 12194875, dated Mar. 11, 2013 (12 pages).

* cited by examiner

HOSPITAL BED HAVING NEAR FIELD COMMUNICATION CAPABILITY

CROSS REFERENCE TO RELATED APPLICATIONS

The present application claims the benefit, under 35 U.S.C. §119(e), of U.S. Provisional Application No. 61/564,466 which was filed Nov. 29, 2011 and which is hereby incorporated by reference herein.

BACKGROUND

The present disclosure relates to connectors having wired and wireless couplings. The present disclosure also relates to apparatus for associating a hospital bed to a location in a healthcare facility or for transferring data between a hospital bed and a network of computer devices in a healthcare facility, but has use in other applications and in other environments as well.

Wireless communication between patient-support devices, such as hospital beds, and a network of a healthcare facility are known. For example, U.S. Pat. No. 7,399,205, which is hereby incorporated by reference herein, discloses the use of wireless communication circuitry in a plug body of a standard AC power plug and a module that is mounted in a room adjacent a standard AC power receptacle or outlet. Having circuitry included in the plug body increases the weight of the plug body and introduces plug retention issues. That is, the added weight of the circuitry in the plug body has a tendency to cause the plug to fall out of the receptacle. Also, in those embodiments of the '205 patent relying on the use of photodiodes for data transfer, the necessary alignment tolerance requirements present issues of their own. Accordingly, there is a need to improve upon the devices of the '205 patent.

SUMMARY

The present invention may comprise one or more of the features recited in the appended claims and/or the following features which, alone or in any combination, may comprise patentable subject matter:

An apparatus may be provided for providing data communication and power to a device located in a room having a power outlet. The apparatus may include a cable that may extend from the device and that may have at one end thereof a plug which may have a plug body. A plurality of prongs may extend from the plug body and may be configured to couple to the power outlet to receive power. The apparatus may further include a first near field communication antenna which may be carried by the plug body. A communication module may be provided and may comprise a second near field communication antenna. The communication module may be located in the room in proximity to the plug. At least one of the first near field communication antenna and the second near field communication antenna may communicate data wirelessly to the other of the first near field communication antenna and the second near field communication antenna.

According to this disclosure, near field communication circuitry may be carried by the device and may be coupled to the first near field communication antenna via at least one conductor that may be routed along the cable. In some embodiments, near field communication circuitry may be carried by the plug body and may be coupled to the first near field communication antenna. The power outlet may comprise, for example, a standard AC power outlet. A DC power outlet is contemplated as an alternative.

In some embodiments, the first near field communication antenna and the second near field communication antenna may be spaced apart by about four centimeters (4 cm) or less when the first near field communication antenna and the second near field communication antenna communicate wirelessly. It is possible, however, for the first and second near field communication antennae to be spaced apart by a greater distance, such as up to 3 inches (7.62 cm) apart, as long as the first and second near field communication antennae are able to successfully receive wireless signals from each other. According to this disclosure, the first near field communication antenna may optionally be included in a label that may stick to the plug body.

In some embodiments, the first near field communication antenna may serve as a passive target and the second near field communication antenna may be coupled to initiator circuitry that may actively generate a radio frequency field via the second near field communication antenna to power up the passive target for data transfer. Alternatively or additionally, the second near field communication antenna may serve as a passive target and the first near field communication antenna may be coupled to initiator circuitry that actively generates a radio frequency field via the first near field communication antenna to power up the passive target for data transfer.

In some embodiments, a wall plate may carry the second near field communication antenna. The wall plate may have an opening through which the power outlet may be accessible. The wall plate carrying the second near field communication antenna may be configured to cover an existing wall plate associated with the power outlet.

According to this disclosure, first circuitry may be coupled to the first near field communication antenna and second circuitry may be coupled to the second near field communication antenna. The first and second circuitry may communicate via the first near field communication antenna and the second near field communication antenna according to a peer-to-peer protocol. In some embodiments, a read/write module may be carried by the plug body and coupled to the first near field communication antenna. Alternatively or additionally, a read/write module may be coupled to the second near field communication antenna.

According to an aspect of this disclosure, an apparatus for coupling a patient-support device to a power outlet and to a computer network in a healthcare facility may be provided. The apparatus may comprise a cable that may extend from the patient-support device and that may have at one end thereof a plug which may comprise a plug body. A plurality of prongs may extend from the plug body and may be configured to couple to the power outlet to receive power. A first near field communication antenna may be carried by the plug body. The apparatus may also have a communication module that may include a second near field communication antenna. At least one of the first near field communication antenna and the second near field communication antenna may communicate data wirelessly to the other of the first near field communication antenna and the second near field communication antenna.

In some embodiments, the communication module may include a housing that may be in close proximity to the power outlet. The second near field communication antenna may be situated in the housing. Optionally, the housing may have an opening through which the plug may be inserted to couple to the power outlet. According to this disclosure, the communication module may comprise a mounting plate that may mount over a cover plate associated with the power outlet. The housing may, in turn, couple to the mounting plate. In some embodiments, the communication module may comprise a Nurse Call cancel button.

According to this disclosure, near field communication circuitry may be carried by the patient-support device and may be coupled to the first near field communication antenna via at least one conductor that may be routed along the cable. In some embodiments, the near field communication circuitry may be carried by the plug body and may be coupled to the first near field communication antenna. According to this disclosure, the first near field communication antenna optionally may be included in a label that may stick to the plug body.

According to an aspect of this disclosure, a system may include a bed having an auxiliary power outlet and a medical device that may include a cable which may have at one end thereof a plug comprising a plug body. A plurality of prongs may extend from the plug body and may couple to the auxiliary power outlet to receive power. The system may have a first near field communication antenna carried by the plug body and a communication module which may have a second near field communication antenna. The communication module may be coupled to the bed in proximity to the auxiliary power outlet. At least one of the first near field communication antenna and the second near field communication antenna may communicate data wirelessly to the other of the first near field communication antenna and the second near field communication antenna.

In some embodiments, the bed may receive data from the medical device via the first and second near field communication antennae. The bed may be configured to send at least some of the data received from the medical device to a unit spaced from the bed. For example, the bed may have a third near field communication antenna and the unit spaced from the bed may have a fourth near field communication antenna. The data sent by the bed may be transmitted from the third near field communication antenna to the fourth near field communication antenna.

According to a further aspect of this disclosure, a system may include a patient support apparatus, a first near field communication module that may be coupled to the patient support apparatus, and a second near field communication module that may be spaced from the patient support apparatus. The first near field communication module may have a first near field communication antenna and the second near field communication module may have a second near field communication antenna. At least one of the first near field communication antenna and the second near field communication antenna may communicate data wirelessly to the other of the first near field communication antenna and the second near field communication antenna. In some embodiments, the first near field communication module retrofits onto the patient support apparatus and the second near field communication module attaches to a surface associated with a room in which the patient support apparatus is located.

Additional features, which alone or in combination with any other feature(s), such as those listed above and those listed in the claims, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures, in which.

DETAILED DESCRIPTION

Figure 1:
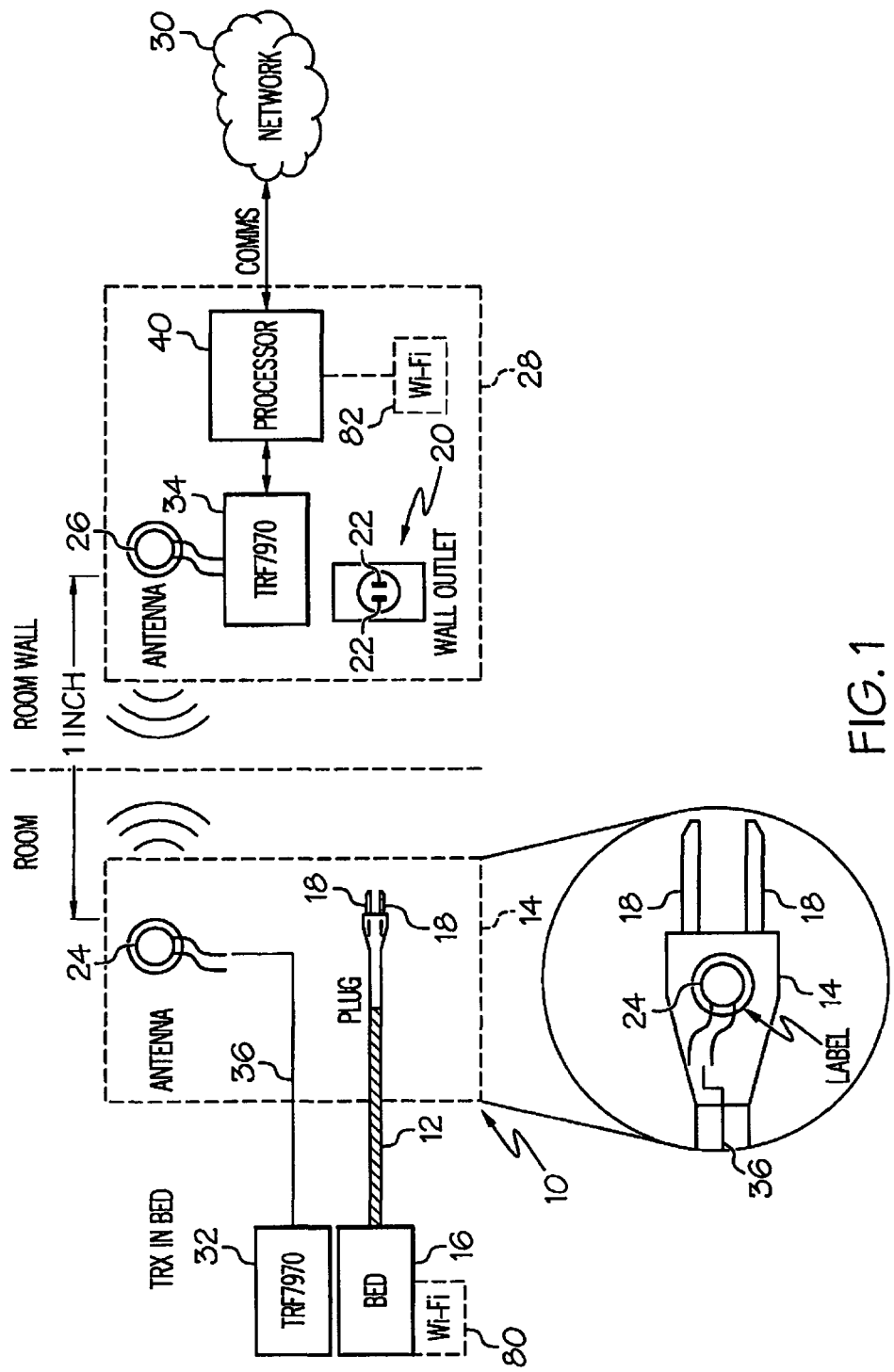
FIG. 1 is a block diagram showing a power cord and plug of a bed having a first near field communication antenna carried by a plug body of the plug, the bed having first near field communication circuitry coupled thereto, and showing a second near field communication antenna and associated second near field communication circuitry included in a module adjacent a wall outlet.

A power plug 10 at the end of a power cord 12 includes a plug body 14 as shown diagrammatically in FIG. 1. Power plug 10 is a standard AC power plug in some embodiments. In other embodiments, plug 10 is a DC power plug. In the illustrative example, cord 12 extends from a patient support apparatus 16, such as a hospital bed, but the teachings of this disclosure are applicable to all devices that receive power via an AC power plug and that transmit or receive data. Such devices may include computers of all types, home appliances, industrial equipment, laboratory equipment, data acquisition equipment, monitoring equipment, musical equipment, telecommunications devices, audio equipment, and video equipment, just to name a few. Plug 10 includes prongs 18 that are received in sockets 22 of a standard AC power outlet or receptacle. The words "outlet" and "receptacle" are used interchangeably in this disclosure.

According to this disclosure, a first near field communication (NFC) antenna 24 is carried by plug body 14 and a second NFC antenna 26 is included in a communication module 28 that is located in proximity to outlet 20. In the illustrative examples of FIGS. 1 and 2, module 26 is coupled to a computer network 30 with which bed 16 communicates. Network 30 includes, for example, computer devices such as nurse call computers, electronic medical records (EMR) computers, admission/discharge/transfer (ADT) computers, and the like in those embodiments in which plug 10 and module 26 is used in the healthcare setting with medical devices such as bed 16. Examples of the type of communication equipment included in various embodiments of a nurse call system (as well as network 30, in general) can be found in U.S. Pat. Nos. 7,746,218; 7,538,659; 7,319,386; 7,242,308; 6,897,780; 6,362,725; 6,147,592; 5,838,223; 5,699,038 and 5,561,412 and U.S. Patent Application Publication Nos. 2009/0217080; 2009/0214009; 2009/0212956; and 2009/0212925, all of which are hereby incorporated by reference herein in their entirety for all that they teach to the extent that they are not inconsistent with the present disclosure which shall control as to any inconsistencies.

Figure 2:
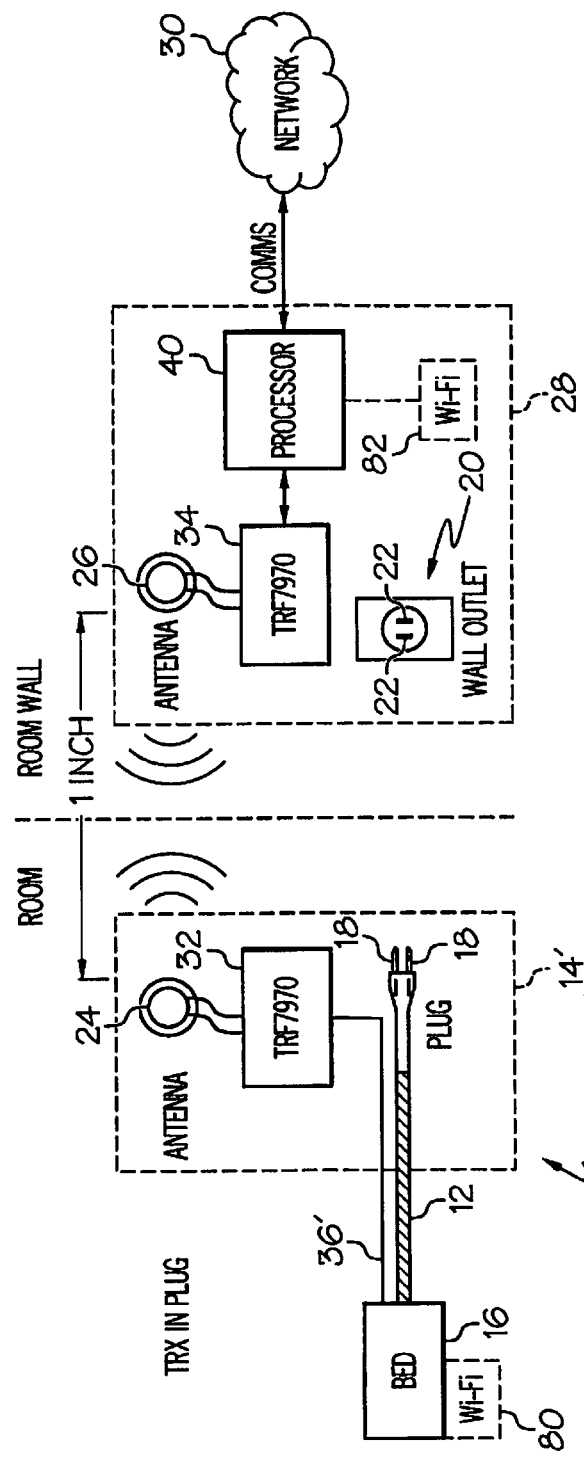
FIG. 2 is a block diagram, similar to FIG. 1, but having both the first near field communication circuitry and first near field communication antenna carried by the plug body.

In the illustrative examples of FIGS. 1 and 2, first NFC antenna 24 is coupled to first near field communication circuitry 32 and second NFC antenna 26 is coupled to second near field communication circuitry 34. In the FIG. 1 embodiment, circuitry 32 is carried by bed 16, such as by being mounted to a bed frame of bed 16, and is coupled to antenna 24 via one or more conductors 36 routed along cable 12. In some embodiments, the power conductors of cable 12 (i.e., the conductors that couple to prongs 18) and conductors 36 are contained within the same cable jacket. Optionally, shielding is provided so as to reduce or eliminate the AC power from interfering with the data signals transmitted over conductors 36. In the FIG. 2 embodiment, circuitry 32 is carried by plug body 14' and is coupled to circuitry of bed 16 via one or more conductors 36' that are routed along cable 12.

Use of NFC antennae 24, 26 and associated circuitry 32, 34 permits simplified transactions, data exchange, and wireless connections between two devices in close proximity to each other, usually by no more than a few centimeters. In the illustrative embodiments of FIGS. 1 and 2, antennae 24, 26 are spaced apart by about 1 inch (2.54 cm). However, suitable results can be achieved with antennae 24, 26 being spaced apart by 4 cm or less. Depending upon the power of circuitry 32, 34 and depending upon the size of antennae 24, 26, a working distance of up to 20 cm may be possible, but in the illustrative embodiments, communication over such a distance is not needed. Thus, near field communication (NFC) is a short-range wireless communication technology. It is known that NFC operates at a frequency of about 13.56 megahertz (MHz) on ISO/IEC 18000-3 air interface and at data transfer rates from about 106 kilobits per second (kbits/s) to about 424 kbits/s.

In the illustrative example, circuitry 32 and circuitry 34 are both powered such that bidirectional, peer-to-peer communication is achieved. In other embodiments, one of antenna 24, 26 and the associated circuitry 32, 34, respectively, serves as an initiator circuit and the other of antenna 24, 26 and associated circuitry 32, 34 serves as a passive target. The initiator actively generates a radio frequency (RF) field that powers the passive target. In such alternative arrangements, the passive targets can be fashioned as tags, stickers, fobs, or cards that do not include batteries or direct connection to external power sources. Thus, according to this disclosure, antenna 24 is included in a label that sticks to plug body 14 (or plug body 14') in some embodiments. Circuitry 32 and/or circuitry 34 are sometimes referred to as read/write modules according to this disclosure.

By having NFC antenna 24 included on plug body 14 (or plug body 14') and by having module 28 located in close proximity to outlet 20, the NFC antennae 24, 26 automatically establish communications quickly in roughly one tenth of a second after plug 10 is plugged into outlet 20. Because plug 10 is configured to receive power and is configured to communicate wirelessly with module 26, only one connector (i.e., plug 10) is needed to provide both power and data to device 16 and furthermore, only this single connector needs to be unplugged if device 16 is to be moved to a new location. Due to the short reception range between antennae 24, 26, the likelihood of unwanted interference from other wireless signals is reduced.

The labels, stickers, or tags that carry the antennae 24, 26 are approximately the size of a U.S. quarter which has a diameter of 24.26 mm (0.955 in) or roughly 1 inch. Thus, in some embodiments, the labels carrying antenna 24 are simply stuck onto plug body 14, 14'. The antenna 24, 26 can be placed up to 10 feet away from a transceiver chip of the associated circuitry 32, 34. Thus, in the FIG. 1 example, conductor 36 has a maximum length of about ten feet. In some embodiments, circuitry 32, 34 includes TRF7970A transceiver boards available from Texas Instruments of Dallas, Tex. By placing the circuitry 32 on bed 16 as shown in the FIG. 1 embodiment, plug body 14 only has the added weight of antenna 24 and a small portion of the length of conductors 36. Thus, plug 10 has less of a tendency to fall out of socket 20 which is an improvement over the embodiments shown and described in U.S. Pat. No. 7,399,205 which is already incorporated herein by reference. Circuitry 32 may be included in an electronics housing mounted on a frame of bed 16, for example. In other embodiments contemplated by this disclosure, however, circuitry 32 is carried by the plug body 14' as shown in FIG. 2.

The module 28 which carries antenna 26 and associated circuitry 34 can be fashioned in any number of ways, including the various embodiments shown in U.S. Pat. No. 7,399,205. For example, module 28 may be fashioned as a wall plate that carries antenna 26 and that has an opening through which the sockets 22 of AC power outlet 20 are accessible for receiving prongs 18 of plug 10. The wall plate carrying the antenna 26 is configured to cover an existing wall plate associated with the AC power outlet 20 in some embodiments. Such an embodiment of a wall plate may be fashioned similarly to the embodiment of FIGS. 1-4 of U.S. Pat. No. 7,399,205, for example.

In other embodiments, the wall plate or module 26 carrying antenna 26 replaces the existing wall plate altogether. In further embodiments, antenna 26 is carried in a housing or plate that mounts to a wall or similar structure in close proximity to outlet 20 but without covering up any of the existing wall plate of the outlet 20. The term "close proximity" is intended to mean close enough that communications between antenna 26 and antenna 24 is possible when plug 10 is coupled to outlet 20. In still other embodiments, antenna is carried in a housing of an adapter module that plugs into outlet 20. The adapter module may be fashioned similar to any of those shown in FIGS. 8-12 of U.S. Pat. No. 7,399,205 for example.

As shown diagrammatically in FIGS. 1 and 2, this disclosure contemplates that circuitry 34 is included in the same module 28 as antenna 26 in some embodiments. In some embodiments, such as the illustrative embodiments, further processor circuitry 40 is also included in module 28. In other embodiments, circuitry 28 and/or circuitry 40 is included in a housing that is separate from the module 28 that carries antenna 26. In such embodiments, a communication cable interconnects the module 28 carrying antenna 26 with the housing or module carrying circuitry 28 and/or circuitry 40.

In some embodiments, module 28 is not connected to network 30 but rather simply serves to provide the circuitry of bed 16 with a location identifier (ID) that is transmitted from antenna 26 to antenna 24. The circuitry of bed 16, in turn, transmits a bed identifier (ID) and the location identifier such as by wireless communications with a wireless access point, for example. In such an embodiment, the wireless access point is coupled to the network 30. Remote computers of the network 30 receive the bed ID and the location ID to associate bed 16 with the location in the healthcare facility at which bed 16 is located. In some embodiments, bed 16 transmits additional data, such as bed status information, patient physiological data, bed diagnostic data, and so forth. In other embodiments, the bed ID and/or the additional data is transmitted via antenna 24 to antenna 26 and then on to network 30 via circuitry 34 and/or circuitry 40. The location ID of module 28 is also transmitted so that the bed-to-room association can be made by remote computers in those embodiments as well.

Examples of the type of bed data that is transmitted from bed 16 via near field communication circuitry 32, 34 and antennae 24, 26 to network 30, for various embodiments of bed 16, is summarized below in Table 1 as follows:

TABLE 1

| | 0x04 Bed Inputs Messages | Description | Bed Type 1 | Bed Type 2 | Bed Type 3 | Bed Type 4 | Bed Type 5 | Bed Type 6 |
|---|---|---|---|---|---|---|---|---|
| Bed Status | | Basic | | | | | | |
| | Brake Status | Brake set, brake not set | X | X | X | X | X | X |
| | Surface Prevent Mode | Not activated, activated | X | X | | | X | X |
| | Bed Exit or PPM Armed | Armed, not armed | X | X | X | X | X | X |
| | Bed Low Position | Bed not down, bed down | X | X | X | X | X | X |
| | Both Headrails Up | Not down, down | X | X | X | X | X | X |
| | Both Footrails Up | Not down, down | X | X | X | X | X | X |
| Enhanced | | PPM | | | | | | |
| Bed Status | PPM Mode - Positioning | Not selected, mode selected | X | X | X | X | | |
| | PPM Mode-Exiting | Not selected, mode selected | X | X | X | X | | |
| | PPM Mode - Patient Out of Bed | Not selected, mode selected | X | X | X | X | | |
| | PPM or Bed Exit Alarming | Alarming, not alarming | X | X | X | X | | |
| | | Rails | | | | | | |
| | Right Headrail Position | Not down, down | | X | X | X | | |
| | Left Headrail Position | Not down, down | | X | X | X | | |
| | Right Footrail Position | Not down, down | | X | X | X | | |
| | Left Footrail Position | Not down, down | | X | X | X | | |
| | | Lockouts | | | | | | |
| | Head Motor Lockout | Not locked, locked | X | X | X | X | | |
| | Knee Motor Lockout | Not locked, locked | X | X | X | X | | |
| | High-Low Motor Lockout | Not locked, locked | X | X | X | X | | |
| | All Motor Lockout | Not locked, locked | X | X | X | X | | |
| | | Wound Surface | | | | | | |
| | Surface Turn Assist Left Mode | Not active, active | X | X | | | | |
| | Surface Turn Assist Right Mode | Not active, active | X | X | | | | |
| | Surface Max Inflate Mode | Not active, active | X | X | | | | |
| | Heel Suspension Mode | Not active, active | X | | | | | |
| | | Pulmonary Surface | | | | | | |
| | Rotation Mode | Not active, active | X | | | | | |
| | Opti-Rest Mode | Not active, active | X | | | | | |
| | Percussion | Not active, active | X | | | | | |
| | Vibration | Not active, active | X | | | | | |
| | | Maintenance Alerts | | | | | | |
| | Battery Status Modes, 2 bits | 0% charged or disconnected | X | X | | | | |
| | | Not fully charged | X | X | | | | |
| | | Battery fully charged | X | X | | | | |
| | AC Power Not Present Mode | AC present, AC not present | X | X | | | | |
| | Service Required Message | Service required, no service required | X | X | X | X | | |
| | | Head Angle Alarm | | | | | | |
| | Head Angle Alarm Armed | Alarm armed, not armed | X | X | | X | | |
| | Head Angle Alarm Alarming | Alarming, not alarming | X | X | | X | | |
| | Head Angle Alarm Suspended | Alarm suspended, not suspended | X | | | | | |
| | | Other Bed Data | | | | | | |
| | CPR Mode | CPR switch active, CPR switch not active | X | X | | | | |
| | AC Power Present Mode | AC present, AC not present | X | X | | | | |
| | Nurse Call Switch | Switch active, switch not active | X | X | X | X | | |
| | Care Alert Switch | Switch active, switch not active | X | X | X | X | | |
| | Chair Mode | Bed in chair mode, not in chair mode | X | | | | | |
| | Head Angle | Variable head angle in degrees | X | X | | X | | |

TABLE 1-continued

| | 0x04 Bed Inputs Messages | Description | Bed Type 1 | Bed Type 2 | Bed Type 3 | Bed Type 4 | Bed Type 5 | Bed Type 6 |
|---|---|---|---|---|---|---|---|---|
| | Patient Weight | Variable patient weight | X | X | X | X | | |
| | Patient Weight - Date | Date stamp, part 1: YYYYMMDD | X | | | | | |
| | Patient Weight-Time | Time stamp, part 2: DDHHMMSS | X | | | | | |
| Bed | Bed Configuration and ID | | | | | | | |
| Configuration & ID | Bed Exit Present | System present, not present | X | | | | | |
| | Prevention Mode Present | System present, not present | X | X | | | | |
| | Bed Position (down) Switch | System present, not present | X | X | X | X | | |
| | Brake Switch | System present, not present | X | X | X | X | | |
| | Footrail Switch(es) | Switch(es) present, not present | X | X | X | X | | |
| | Headrail Switch(es) | Switch(es) present, not present | X | X | X | X | | |
| | Nurse Call Switch | Nurse Call switch present, no Nurse Call | X | X | X | X | | |
| | PPM Module Installed | PPM present, not present | | X | X | X | | |
| | Scale Module Installed | Scale present, not present | X | X | X | X | | |
| | Dynamic Surface Installed | Air present, not present | X | X | | | | |
| | Enhanced Bed Status Protocol | Enhanced Bed Status supported, not supported | X | X | X | X | | |
| | Rotation Module Installed | Module present, not present | X | | | | | |
| | Perc/Vib Module Installed | Module present, not present | X | | | | | |
| | Bed Serial Number | Side Com board serial number | X | X | X | X | | |
| | Bed ID | Type and revision of bed | X | X | X | X | | |

In the example of Table 1, Bed Type 1 is the TOTAL-CARE® bed, Bed Type 2 is the VERSACARE® bed, Bed Type 3 is the CAREASSIST® ES bed, Bed Type 4 is the ADVANTA™ 2 bed, Bed Type 5 is the ADVANCE bed, and Bed Type 6 is the ADVANTA bed, each of which is, or was, marketed by Hill-Rom Company, Inc. Beds 16 of other types which have other types of bed data are, of course, within scope of this disclosure. Based on Table 1, it will be appreciated that bed data includes, for example, data pertaining to one or more of the following: a position of one portion of a bed frame relative to another portion of the bed frame (e.g., Brake Status, Bed Low Position, Rail positions, Head Angle), a mattress function (e.g., Wound Surface and Pulmonary Surface information), a status of a bed exit alarm system of the hospital bed (e.g., the patient position monitoring (PPM) information), and patient physiologic data (e.g., patient weight). It is also contemplated by this disclosure that maintenance and/or service data is among the type of bed data that is transmitted from bed 16 via near field communication circuitry 32, 34 and antennae 24, 26 to network 30, for various embodiments of bed 16.

In some contemplated embodiments, bed 16 has a mattress and/or bed frame with sensors to sense patient physiologic data (e.g., heart rate, temperature, respiration rate, blood oxygenation, blood pressure, etc.) and that such data is also among the bed data communicated from bed 16 to circuitry 32 and antenna 24 and then on to network 30 via antenna 26 and circuitry 34. An example of a mattress with physiologic sensors can be found in U.S. Pat. Nos. 7,515,059; 7,330,127 and 6,721,980 which are hereby incorporated by reference herein for all that they teach to the extent they are not inconsistent with the present application which shall control as to any inconsistencies. Other examples of mattresses and bed frames having physiologic sensors can be found in U.S. Patent Application Publication No. 2010/0101022 which is hereby incorporated by reference for all that it teaches to the extent that it is not inconsistent with the present application which shall control as to any inconsistencies.

Figure 3:
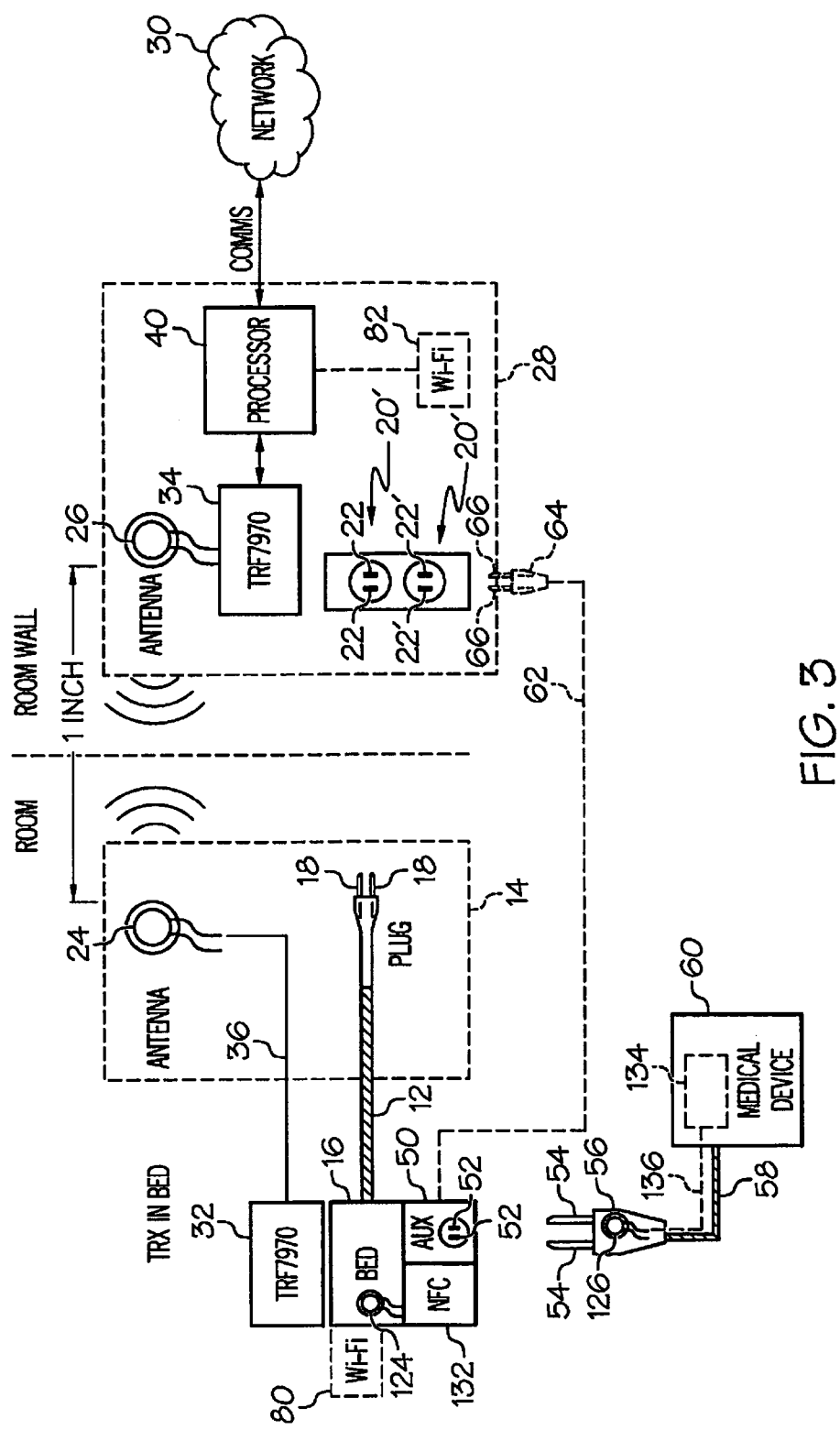
FIG. 3 is a block diagram, similar to FIG. 1, but having an auxiliary power outlet mounted to the bed and additional near field communication antennae and circuitry provided on the bed and on a medical device that receives power from the auxiliary power outlet.

Referring now to FIG. 3, an embodiment is shown in which bed 16 includes an auxiliary power outlet 50 which has sockets 52 that receive prongs 54 of a plug 56 provided at the end of a power cord 58 extending from a medical device 60. Medical device 60 may comprise any type of medical device used for providing care to a patient or used in monitoring a patient physiological condition, for example. Thus, examples of some medical devices 60 within the scope of this disclosure include IV pumps, blood pressure monitors, electrocardiographs (EKG's), electroencephalographs (EEG's), pulse oximeters, ventilators, respiration monitors, and temperature monitors, just to name a few.

In some embodiments, power is provided to auxiliary outlet 50 from power cord 12. In such embodiments, isolation circuitry is included in bed 16 so as to isolate bed power from the auxiliary power. In other embodiments, a separate power cord 62 extends from bed 16 and has a plug 64 with prongs 66 that are received in sockets of a power outlet. In the illustrative example of FIG. 3, power cord 62 is shown diagrammatically via a dotted line and prongs 66 of plug 64 are shown arranged for coupling to sockets 22' of a duplex power outlet 20'. Thus, in this alternative embodiment, power cord 62 and auxiliary outlet 50 are not electrically coupled in any way to the circuitry of bed 16, but rather bed 16 serves as a carrier for auxiliary outlet 50. It is within the scope of this disclosure for bed 16 to have more than one auxiliary outlet 50. Thus, the discussion below of near field communication capability associated with one auxiliary outlet 50 is equally applicable for each auxiliary outlet of a bed having multiple such outlets.

According to this disclosure, bed 16 has an additional near field communication antenna 124 and additional near field communication circuitry 132 in close proximity to auxiliary outlet 50 as shown diagrammatically in FIG. 3. Antenna 124 communicates wirelessly with a further near field communication antenna 126 provided on plug 56. In some embodiments, antenna 126 is included as part of a passive circuit carried by a label coupled to plug 56. In such embodiments, after the passive circuitry has been activated by circuitry 132 of bed 16 via antenna 124, medical device identification (ID) data is transmitted via antenna 126 to antenna 124 to confirm that a proper device has been plugged into the auxiliary outlet 50.

If it is determined by circuitry of bed 16 that an inappropriate or wrong device has been plugged into outlet 50, then bed 16 transmits an appropriate alert message to network 30 and, in some embodiments, disconnects power from auxiliary outlet 50 so as to turn off medical device 60. In some embodiments, bed 16 includes a visual indicator of some sort, such as a message on a graphical display screen or an alert light, to indicate locally that an inappropriate device has been connected to auxiliary outlet 50. Thus, according to this disclosure, bed 16 is configurable such that its one or more auxiliary outlets 50 are designated for specific pieces or equipment or specific types of equipment. The near field communication capability of bed 16 associated with the auxiliary outlet(s) 50 are used to verify that the designated equipment is coupled to outlet(s) 50. In some embodiments, bed 16 interacts with and/or controls device 60 via data transmitted via antennae 124, 126. For example, a touch screen display on bed 16 is configured to accept user inputs for controlling device 60 in some embodiments.

In many hospitals and other types of healthcare facilities, there are two separate power grids, one being a critical power grid and the other being a non-critical power grid. Outlets associated with the critical power grid are typically indicated by being red or orange in color and outlets associated with non-critical power grid are typically white or off white in color. During a power outage or other emergency in which power to a hospital or healthcare facility is lost, one or more generators are usually operated to provide back-up power to the critical power grid. It is desirable, therefore, that only critical devices, such as ventilators, infusion pumps, and other devices that provide critical care (e.g., life sustaining care) to a patient are connected to outlets associated with the critical power grid so that non-critical devices do not need to be powered by the back-up generators during an emergency or power outage. Thus, according to this disclosure, near field communication components 124, 126, 132, 134 are used to make sure that only medical devices 60 that are deemed critical (i.e., the appropriate or proper medical devices) are used with the one or more auxiliary outlets 50 of bed 16.

In some embodiments, medical devices 60 include near field communication circuitry 134 which is coupled to antenna 126 via conductors 136 as indicated diagrammatically. Circuitry 134 is used for transmitting medical device data to the circuitry of bed 16 via antennae 126, 124 and circuitry 132. Alternatively or additionally, bed data is transmitted to medical device 60 via circuitry 132, 134 and antennae 124, 126. For example, if device 60 is an infusion pump or drug delivery pump, then bed 16 may transmit patient weight data to device 60 which, in turn, may use the patient weight data to establish a rate at which a fluid or drug is administered to the associated patient. As another example, if device 60 senses that its fluid level is running low, then that information may be communicated to bed 16 which, in turn, transmits an alert message to a remote computer device of network 30, including transmission to a portable wireless communication device carried by a caregiver. Alternatively or additionally, a local alert regarding the alert condition of device 60 is displayed locally on bed 16, such as being displayed on a display screen. Circuitry 134 is shown as being carried by medical device 60 in FIG. 3, however, in other embodiments, circuitry 134 is carried by plug 56.

In the illustrative example of FIG. 3, data communicated to bed 16 from device 60 via near field communication components 124, 126, 132, 134 is subsequently transmitted to network via near filed communication components 24, 26, 32, 34. In other embodiments, near filed communication components 24, 26, 32, 34 are omitted and bed transmits data received from device 60 to network 30 via some other wireless communication scheme, such as Wi-Fi communication to a wireless access point, for example, or via a wired connection to network 30. Thus, according to an aspect of this disclosure, bed 16 in each of the FIG. 1-3 examples is shown as having optional Wi-Fi circuitry 80 and module 28 is shown as having Wi-Fi circuitry 82. Further aspects of Wi-Fi circuitry 80, 82 is discussed below.

According to an aspect of this disclosure, the near field communication components 24, 26, 32, 34 may serve as a secondary or back-up communication channel between bed 16 and remote computer devices of network 30. Thus, bed 16 may couple to network 30 via a separate nurse call cable, such as a 37-pin cable typically used to connect Hill-Rom beds to a nurse call system, which serves as the primary communication channel for data to and from bed 16. In such embodiments, the primary nurse call channel operates at faster data transfer rates than the data transfer rate at which near field communication components 24, 26, 32, 34 operate. In still other embodiments, near field communication components 24, 26, 32, 34 are used for determining bed-to-room location and then bed uses another communications channel, such as a wired connection or wi-fi to wireless access point communication, as the primary communication channel.

According to another embodiment, antenna 24 is not mounted on plug 14 but instead, is coupled to some other portion of bed 16. For example, antenna 24 is mounted on a base frame of bed 16 in some embodiments. In such embodiments, antenna 26 and its associated circuitry 34 need not be placed near any wall outlet. In this embodiment, the near field communication components 24, 26, 32, 34 operate as a bed docking system which is used for establishing bed-to-room association. The near filed communication components 24, 32 may be included in a module that bolts onto, or otherwise mounts, to bed 16 and then components 26, 34 are wall mounted and wired to network 30. This allows for retrofitting existing beds with near field communication components 26, 34, again, for bed-to-room association purposes. The term "wall mounted" is intended to encompass mounting onto a room wall or onto a portion of some other piece of architectural equipment (e.g., headwall units, columns, arms, carts, chases, bed locators) found in a patient room, as well as mounting on a floor or ceiling. The term wall outlet is intended to cover power outlets mounted to room walls and power outlets mounted on other architectural equipment, a ceiling, or a floor.

According to another aspect of this disclosure, the Wi-Fi circuitry 80, 82 is used to support secondary radio communications, such as voice communications or entertainment (e.g., television or radio) audio signal communications, to and from bed 16. In some embodiments, Wi-Fi circuitry 80, 82 operates according to the Bluetooth protocol, although any suitable wireless technology is within the scope of this disclosure. In some embodiments, the Wi-Fi circuitry 80, 82 uses bed ID and location ID transmitted via antennae 24, 26 to automatically pair up for the secondary radio communications. However, this need not be the case if circuitry 80, 82 is operable to perform the automatic pairing functions themselves. Thus, to give an example, a patient on bed 16 communicates with a caregiver at a remote nurse's station by pressing a nurse call button or switch as is known in the art. The patient's voice is picked up by a microphone on bed 16 and transmitted to the remote nurse's station via circuitry 80, 82 and the caregiver's voice is heard by the patient through a speaker on bed 16 that receives the caregiver's voice audio via circuitry 80, 82. Of course, other circuitry and components, such as network 30 and processor 40 are included in the audio data link between the bed 16 and remote nurse's station in some embodiments.

Also according to this disclosure, bed 16 configures itself differently based on location ID data transmitted via antenna 26 from module 28 and received by antenna 24. For example, if the location ID indicates that the bed 16 is located in a med/surg room (e.g., a typical patient room) the bed 16 configures its settings in one way and if the location ID indicates that the bed is located in the intensive care unit (ICU), the bed 16 configures its setting in another way. Some screens that are shown on the graphical user interface of bed 16 for control of various features of bed 16 may be enabled or disabled depending upon the location of bed 16. Further according to this disclosure, patient ID data is transmitted from a remote computer of network 30 to bed 16 via antennae 24, 26 and bed 16 configures itself based on patient ID. For example, certain therapies such as continuous lateral rotation therapy (CLRT), alternating pressure therapy, low air loss therapy, and the like may be indicated for the particular patient and bed 16 will enable the appropriate therapy based on the patient ID. Therapies that may be contraindicated, such as, CLRT for a spinal surgery patient, are disabled by bed 16 based on patient ID.

In some embodiments, the location ID is used by the bed 16 to configure room lighting or to determine the type of television in the room and so forth. It is further contemplated that in some embodiments, the location ID is used by bed 16 to enable features such as permitting a patient to order and pay for video on demand or to turn on features of a rental bed or to gain access to remote servers or websites for looking up medical information. Data communicated between antenna 24 of bed 16 and antenna 26 of module 28 is used, in some embodiments, to synchronize display of data from devices 60 on a display of bed 16, or vice versa, and even to provide display information to mobile devices carried by caregivers.

Although certain illustrative embodiments have been described in detail above, many embodiments, variations and modifications are possible that are still within the scope and spirit of this disclosure as described herein and as defined in the following claims.

The invention claimed is:

1. An apparatus for providing data communication and power to a device located in a room, the room having a power outlet, the apparatus comprising
    a cable extending from the device and having at one end thereof a plug comprising a plug body, a plurality of prongs extending from the plug body and configured to couple to the power outlet to receive power,
    a first near field communication antenna carried by the plug body,
    near field communication circuitry carried by the device and coupled to the first near field communication antenna via at least one conductor routed along the cable, wherein the plug body is devoid of any circuit components of the near field communication circuitry, and
    a communication module comprising a second near field communication antenna, the communication module being located in the room in proximity to the plug, at least one of the first near field communication antenna and the second near field communication antenna communicating data wirelessly to the other of the first near field communication antenna and the second near field communication antenna, wherein the first near field communication antenna is included in a label that sticks to the plug body, wherein the label is devoid of any electrical components other than the antenna and at least one conductor leading to the antenna.

2. The apparatus of claim 1, wherein the first near field communication antenna and the second near field communication antenna are spaced apart by about four centimeters (4 cm) or less when the first near field communication antenna and the second near field communication antenna communicate wirelessly.

3. The apparatus of claim 1, wherein the first near field communication antenna serves as a passive target and the second near field communication antenna is included as part of an initiator circuit that actively generates a radio frequency field via the second near field communication antenna to power up the passive target for data transfer.

4. The apparatus of claim 1, wherein the second near field communication antenna serves as a passive target and the first near field communication antenna included as part of an initiator circuit that actively generates a radio frequency field via the first near field communication antenna to power up the passive target for data transfer.

5. The apparatus of claim 1, further comprising a wall plate carrying the second near field communication antenna and the wall plate having an opening through which the power outlet is accessible.

6. The apparatus of claim 1, further comprising a wall plate carrying the second near field communication antenna and the wall plate being configured to cover an existing wall plate associated with the power outlet.

7. The apparatus of claim 1, further comprising first circuitry coupled to the first near field communication antenna and second circuitry coupled to the second near field communication antenna, the first and second circuitry communicating via the first near field communication antenna and the second near field communication antenna according to a peer-to-peer protocol.

8. The apparatus of claim 1, further comprising a read/write module coupled to the first near field communication antenna.

9. The apparatus of claim 1, further comprising a read/write module coupled to the second near field communication antenna.

10. An apparatus for coupling a patient-support device to a power outlet and to a computer network in a healthcare facility, the apparatus comprising
- a cable extending from the patient-support device and having at one end thereof a plug comprising a plug body, a plurality of prongs extending from the plug body and configured to couple to the power outlet to receive power, and a first near field communication antenna carried by the plug body,
- near field communication circuitry carried by the patient-support device and coupled to the first near field communication antenna via at least one conductor routed along the cable, wherein the plug body is devoid of any circuit components of the near field communication circuitry,
- a communication module comprising a second near field communication antenna, at least one of the first near field communication antenna and the second near field communication antenna communicating data wirelessly to the other of the first near field communication antenna and the second near field communication antenna, wherein the first near field communication antenna is included in a label that sticks to the plug body, wherein the label is devoid of any electrical components other than the antenna and at least one conductor leading to the antenna.

11. The apparatus of claim 10, wherein the communication module comprises a housing in close proximity to the power outlet and the second near field communication antenna is situated in the housing.

12. The apparatus of claim 11, wherein the housing has an opening through which the plug is inserted to couple to the power outlet.

13. The apparatus of claim 11, wherein the communication module further comprises a mounting plate that mounts over a cover plate associated with the power outlet and the housing couples to the mounting plate.

14. The apparatus of claim 10, wherein the communication module comprises a Nurse Call cancel button.

* * * * *

UNITED STATES PATENT AND TRADEMARK OFFICE
CERTIFICATE OF CORRECTION

PATENT NO. : 9,466,877 B2
APPLICATION NO. : 13/687005
DATED : October 11, 2016
INVENTOR(S) : Steven A. Dixon et al.

Page 1 of 1

It is certified that error appears in the above-identified patent and that said Letters Patent is hereby corrected as shown below:

In the claims

Col. 14, Line 43, the word --is-- is added after the word "antenna."

Signed and Sealed this
Twentieth Day of December, 2016

Michelle K. Lee
*Director of the United States Patent and Trademark Office*